US011993577B2

(12) United States Patent
Fawaz et al.

(10) Patent No.: US 11,993,577 B2
(45) Date of Patent: *May 28, 2024

(54) SYNTHESIS OF MDMA OR ITS OPTICALLY ACTIVE (R)- OR (S)-MDMA ISOMERS

(71) Applicant: EmpathBio, Inc., Encinitas, CA (US)

(72) Inventors: Majed Fawaz, Foxborough, MA (US); Nicholas Morra, Ontario (CA)

(73) Assignee: EmpathBio, Inc., Encinitas, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/901,504

(22) Filed: Sep. 1, 2022

(65) Prior Publication Data
US 2023/0096116 A1 Mar. 30, 2023

Related U.S. Application Data

(60) Provisional application No. 63/239,853, filed on Sep. 1, 2021.

(51) Int. Cl.
C07D 317/58 (2006.01)

(52) U.S. Cl.
CPC .................. C07D 317/58 (2013.01)

(58) Field of Classification Search
CPC .................. C07D 317/58
USPC ...................... 549/440
See application file for complete search history.

(56) References Cited

U.S. PATENT DOCUMENTS

| | | | |
|---|---|---|---|
| 3,907,864 | A | 9/1975 | Biel et al. |
| 4,017,636 | A | 4/1977 | Jones et al. |
| 4,937,360 | A | 6/1990 | Liu et al. |
| 5,061,727 | A | 10/1991 | Bloom et al. |
| 5,932,749 | A | 8/1999 | Li et al. |
| 9,907,812 | B2 | 3/2018 | Bapat et al. |
| 2003/0171303 | A1 | 9/2003 | Gallop et al. |
| 2003/0207884 | A1 | 11/2003 | Haap et al. |
| 2005/0130244 | A1 | 6/2005 | Zheng et al. |
| 2006/0035863 | A1 | 2/2006 | Barbeau |
| 2006/0205779 | A1 | 9/2006 | Mu et al. |
| 2006/0205946 | A1 | 9/2006 | Ji et al. |
| 2007/0027208 | A1 | 2/2007 | Caron et al. |
| 2008/0045588 | A1 | 2/2008 | Gant et al. |
| 2008/0146567 | A1 | 6/2008 | Kolczewski et al. |
| 2008/0293695 | A1 | 11/2008 | Bristol et al. |
| 2009/0111741 | A1 | 4/2009 | Aldrich et al. |
| 2010/0137428 | A1 | 6/2010 | Bozzoli et al. |
| 2018/0243241 | A1 | 8/2018 | Popp et al. |
| 2021/0145851 | A1 | 5/2021 | Stamets |
| 2021/0332012 | A1 | 10/2021 | Olson et al. |
| 2022/0151986 | A1 | 5/2022 | Liechti et al. |
| 2022/0267252 | A1 | 8/2022 | Trachsel et al. |
| 2022/0354822 | A1 | 11/2022 | Barrow et al. |
| 2023/0097530 | A1 | 3/2023 | Short et al. |
| 2023/0109467 | A1 | 4/2023 | Anzalone et al. |
| 2023/0129723 | A1 | 4/2023 | Short et al. |
| 2023/0227420 | A1 | 7/2023 | Rao et al. |
| 2023/0227421 | A1 | 7/2023 | Perni et al. |
| 2023/0278977 | A1 | 9/2023 | Fawaz et al. |

FOREIGN PATENT DOCUMENTS

| | | |
|---|---|---|
| CN | 101822841 A | 9/2010 |
| EP | 2687854 A1 | 1/2014 |
| WO | WO-2005038049 A2 | 4/2005 |
| WO | WO-2007090733 A1 | 8/2007 |
| WO | WO-2008033351 A2 | 3/2008 |
| WO | WO-2009049233 A1 | 4/2009 |
| WO | WO-2009095479 A2 | 8/2009 |
| WO | WO-2012177986 A2 | 12/2012 |
| WO | WO-2014013063 A1 | 1/2014 |
| WO | WO-2017147375 A1 | 8/2017 |
| WO | WO-2020077217 A1 | 4/2020 |
| WO | WO-2020101543 A1 | 5/2020 |
| WO | WO-2020252384 A1 | 12/2020 |
| WO | WO-2021252538 A2 | 12/2021 |
| WO | WO-2022006192 A1 | 1/2022 |
| WO | WO-2022010937 A1 | 1/2022 |
| WO | WO-2022032147 A1 | 2/2022 |
| WO | WO-2022053696 A1 | 3/2022 |
| WO | WO-2022061242 A1 | 3/2022 |
| WO | WO-2022106947 A1 | 5/2022 |
| WO | WO-2022150525 A1 | 7/2022 |
| WO | WO-2022182602 A2 | 9/2022 |
| WO | WO-2022235530 A1 | 11/2022 |
| WO | WO-2022256720 A2 | 12/2022 |
| WO | WO-2023034510 A1 | 3/2023 |
| WO | WO-2023044027 A1 | 3/2023 |
| WO | WO-2023056102 A1 | 4/2023 |
| WO | WO-2023056472 A1 | 4/2023 |
| WO | WO-2023129958 A2 | 7/2023 |

OTHER PUBLICATIONS

Acquas et al., J. Neurochem. (2007) vol. 102 pp. 121-132.*
Clouting, H., "The Commercial Chemistry of MDMA: From Research to Patient Access," MAPS Bulletin Special Edition, Spring 2020, pp. 8-10.
Heather, E., "The Synthesis and Chemical Profiling of 3,4-Methylenedioxymethamphetamine (MDMA) and Analogues," Thesis, University of Technology Sydney, Oct. 2020, 232 pages.
Huot et al., "Characterization of 3,4-Methylenedioxymethamphetamine (MDMA) Enantiomers In Vitro and in the MPTP-Lesioned Primate: R-MDMA Reduces Severity of Dyskinesia, Whereas S-MDMA Extends Duration of ON-Time," The Journal of Neuroscience, May 11, 2011, 31(19):7190-7198.
Nenajdenko et al., "A new convenient approach to chiral β-aryl(heteroaryl)alkylamines," Tetrahedron: Asymmetry (2001) 12: 2517-2527.
Rasmussen et al., "Chiral separation and quantification of R/S-amphetamine, R/S-methamphetamine, R/S-MDA, R/S-MDMA, and R/S-MDEA in whole blood by GC-EI-MS," Journal of Chromatography B, (2006) 842: 136-141.
Baker, et al., Critical evaluation of methodology commonly used in sample collection, storage and preparation for the analysis of pharmaceuticals and illicit drugs in surface water and wastewater by solid phase extraction and liquid chromatography-mass spectrometry, Journal of Chromatography A, 2011, pp. 8036-8059.

(Continued)

Primary Examiner — Taofiq A Solola
(74) Attorney, Agent, or Firm — Cooley LLP

(57) ABSTRACT

Provided herein is a process for the preparation of 3,4-methylenedioxymethamphetamine, (R)-3,4-methylenedioxymethamphetamine and (S)-3,4-methylenedioxymethamphetamine.

32 Claims, No Drawings

(56) References Cited

OTHER PUBLICATIONS

Baker, et al., Drugs of abuse in wastewater and suspended particulate matter—Further developments in sewage epidemiology, Environment International, 2012, pp. 28-38.
Baker, et al., Multi-residue analysis of drugs of abuse in wastewater and surface water by solid-phase extraction and liquid chromatography-positive electrospray ionisation tandem mass spectrometry, Journal of Chromatography A, 2011, pp. 1620-1631.
Baker, et al., Multi-residue determination of the sorption of illicit drugs and pharmaceuticals to wastewater suspended particulate matter using pressurized liquid extraction, solid phase extraction and liquid chromatography coupled with tandem mass spectrometry, Journal of Chromatography A, Nov. 2011, pp. 7901-7913.
Barreiro, J.C., et al., "A High-Resolution Magic Angle Spinning NMR Study of the Enantiodiscrimination of 3,4-Methylenedioxymethamphetamine (MDMA) by an Immobilized Polysaccharide-Based Chiral Phase", PLoS ONE, vol. 11, No. 9, Sep. 26, 2016, pp. 1-11.
Castrignano, et al., Enantiomeric profiling of chiral drug biomarkers in wastewater with the usage of chiral liquid chromatography coupled with tandem mass spectrometry, Journal of chromatography A, Mar. 2016, pp. 84-99.
Castrignano, et al., Enantiomeric profiling of chiral illicit drugs in a pan—European study, Water Research, Mar. 2017, 56 pages.
Chen, et al., Investigation of the relationship between phenol ionization and affinity of norepinephrine for adrenergic receptors using ring-fluorinated analogs, Medicinal Chemistry Research, 1994, pp. 589-597.
Chen, et al., Syntheses of 2,5- and 2,6-difluoronorepinephrine, 2,5-difluoroepinephrine, and 2,6-difluorophenylephrine: effect of disubstitution with fluorine on adrenergic activity, Journal of Medicinal Chemistry, 1993, pp. 3947-3955.
Collins, et al., Identification and characterization of N-tert-butoxycarbonyl-MDMA: a new MDMA precursor, Drug Testing and Analysis, Mar. 2017, pp. 399-404.
Corkery, et al., Deaths in the Lesbian, Gay, Bisexual and Transgender United Kingdom Communities Associated with GHB and Precursors, Current drug metabolism, Nov. 2018, pp. 1086-1099.
Crean, R.D., et al., "Oral Administration of (±)3,4-Methylenedioxymethamphetamine and (+) Methamphetamine Alters Temperature and Activity in Rhesus Macaques", Pharmacol Biochem Behav, vol. 87, No. 1, Authors Manuscript PMC May 1, 2008, pp. 1-18.
Curry et al., "Separating the agony from ecstasy: R(−)-3,4-methylenedioxymethamphetamine has prosocial and therapeutic-like effects without signs of neurotoxicity in mice," Neuropharmacology. Jan. 2018 ; 128: 196-206, 26 pages.
Deluca, et al., Searching the Internet for drug-related web sites: analysis of online available information on ecstasy (MDMA), American Journal on Addictions, Nov. 2007, 5 pages.
Dunlap et al., "Dark Classics in Chemical Neuroscience: 3,4-Methylenedioxymethamphetamine (MDMA)," ACS Chem Neurosci. Oct. 17, 2018; 9(10): 2408-2427, 46 pages.
Eiden, et al., VMAT2: a dynamic regulator of brain monoaminergic neuronal function interacting with drugs of abuse, Ann N Y Acad Sci., Jan. 2011, pp. 86-98.
Fallon et al., "Stereospecific Analysis and Enantiomeric Disposition of 3,4-Methylenedioxymethamphetamine (Ecstasy) in Humans," Clinical Chemistry (1999) 45:7, 1058-1069.
Fantegrossi, et al., 3, 4-Methylenedioxymethamphetamine (MDMA, "ecstasy") and its stereoisomers as reinforcers in rhesus monkeys: serotonergic involvement, Psychopharmacology, Jun. 2002, pp. 56-64.
Fantegrossi et al., "Pharmacological characterization of the effects of 3,4-methylenedioxymethamphetamine ("ecstasy") and its enantiomers on lethality, core temperature, and locomotor activity in singly housed and crowded mice," Psychopharmacology (2003) 166: 202-211.
Fantegrossi, In vivo pharmacology of MDMA and its enantiomers in rhesus monkeys, Experimental and clinical psychopharmacology, Feb. 2008, 1 page.
Felim et al., "Synthesis and in Vitro Cytotoxicity Profile of the R-Enantiomer of 3,4-Dihydroxymethamphetamine (R-(−)-HHMA): Comparison with Related Catecholamines," Chem. Res. Toxicol. 2010, 23, 211-219.
Filler, et al., Fluorine-containing catecholamines. Synthesis of DL-2,5,6-trifluorodopa, Journal of Fluorine Chemistry, 1981, pp. 483-495.
Fitzgerald, et al., Stereoselective pharmacokinetics of 3,4-methylenedioxymethamphetamine in the rat, Chirality, 1990, pp. 241-248.
Forsling, et al., The effect of 3,4-methylenedioxymethamphetamine (MDMA,'ecstasy') and its metabolites on neurohypophysial hormone release from the isolated rat hypothalamus, British Journal of Pharmacology, Feb. 2002, pp. 649-656.
Hagele, et al., Enantioselective separation of Novel Psychoactive Substances using a Lux® AMP 3 µm column and HPLC-UV. Journal of Pharmaceutical and Biomedical Analysis, Feb. 2020, 2 pages.
Han, et al., Comparison of the monoamine transporters from human and mouse in their sensitivities to psychostimulant drugs, BMC Pharmacology, Dec. 2006, pp. 1-7.
Hensley, et al., Simultaneous determination of amphetamine, methamphetamine, methylenedioxyamphetamine (MDA), methylenedioxymethamphetamine (MDMA), and methylenedioxyethylamphetamine (MDEA) enantiomers by GC-MS, Journal of Analytical Toxicology, Oct. 1999, pp. 518-523.
Herr, et al., Re-evaluation of the discriminative stimulus effects of lysergic acid diethylamide with male and female Sprague-Dawley rats, Behavioral Pharmacology, Sep. 2020, pp. 776-786.
Hiramatsu, et al., Enantiomeric differences in the effects of 3, 4-methylenedioxymethamphetamine on extracellular monoamines and metabolites in the striatum of freely-moving rats: an in vivo microdialysis study, Neuropharmacology, Mar. 1990, pp. 269-275.
International Search Report and Written Opinion for International Application No. PCT/US2022/043833 dated Jan. 12, 2023, 13 pages.
International Search Report and Written Opinion for International Application No. PCT/US2022/082468, dated Jun. 6, 2023, 11 pages.
Invitation to Pay Fee for International Application No. PCT/US2022/045587 dated Nov. 18, 2022, 3 pages.
Invitation to Pay for International Application No. PCT/US2022/082468 dated Mar. 16, 2023, 2 pages.
Johnson et al., Effects of enantiomers of MDA, MDMA and related analogues on [3H] serotonin and [3H] dopamine release from superfused rat brain slices, European Journal of Pharmacology, 1986, pp. 269-276.
Kilpatrick, et al., National estimates of exposure to traumatic events and PTSD prevalence using DSM-IV and DSM-5 criteria, Journal of Traumatic Stress, Oct. 2013, pp. 537-547.
Kozma, D., et al., "Optical resolution of N-methylamphetamine via diastereoisomeric salt formation with 2R,3R-O,O'-di-p-toluoyltartaric acid," Chirality, 1999, vol. 11, Issue 5-6, pp. 373-375.
Ladd, et al., Improved synthesis of fluoroveratroles and fluorophenethylamines via organolithium reagents, Journal of Organic Chemistry, 1981, pp. 203-206.
Leapman, et al., Application of parallel recorded EELS to analysis of beam-sensitive organic compounds, Biomed. Eng. Instrum., Proceedings—Annual Meeting, Electron Microscopy Society of America, 1988, pp. 632-633.
Leapman, et al., Applications of electron energy loss spectroscopy in biology: detection of calcium and fluorine, Proceedings—Annual Meeting, Electron Microscopy Society of America, 1982, pp. 412-415.
Levine et al. (editor), "Principles of Forensic Toxicology," Springer, Fifth Edition, 2020, 680 pages.
Liabres et al., Molecular basis of the selective binding of MDMA enantiomers to the alpha4beta2 nicotinic receptor subtype: synthesis, pharmacological evaluation and mechanistic studies, European Journal of Medicinal Chemistry, Jun. 2014, pp. 35-46.

(56) References Cited

OTHER PUBLICATIONS

Lourenco et al., Chiral separation of 3,4-methylenedioxymethamphetamine (MDMA) enantiomers using batch chromatography with peak shaving recycling and its effects on oxidative stress status in rat liver, Journal of Pharmaceutical and Biomedical Analysis, Jan. 2013, pp. 13-17.
Madry, et al., Evaluation of drug incorporation into hair segments and nails by enantiomeric analysis following controlled single MDMA intakes, Analytical and Bioanalytical Chemistry, Jan. 2016, pp. 545-556.
Martins, et al., Simultaneous enantioselective determination of amphetamine and congeners in hair specimens by negative chemical ionization gas chromatography-mass spectrometry, Journal of Chromatography B, Oct. 15, 2005, pp. 57-62.
Martins, et al., Time-resolved hair analysis of MDMA enantiomers by GC/MS-NCI, Forensic Science International, Oct. 2007, pp. 150-155.
Mas, et al., Cardiovascular and neuroendocrine effects and pharmacokinetics of 3,4-methylenedioxymethamphetamine in humans, Journal of Pharmacology and Experimental Therapeutics, Jul. 1, 1999, pp. 136-145.
Matsushima, et al., Optical isomer analysis of 3,4-methylenedioxyamphetamine analogues and their stereoselective disposition in rats, Journal of Analytical Toxicology, Jan. 1998, pp. 33-39.
Milhazes, et al., Electrochemical and spectroscopic characterisation of amphetamine-like drugs: Application to the screening of 3,4-methylenedioxymethamphetamine (MDMA) and its synthetic precursors, Analytica Chimica Acta, 2007, pp. 231-241.
Murnane, et al., Discriminative stimulus effects of psychostimulants and hallucinogens in S (+)-3, 4-methylenedioxymethamphetamine (MDMA) and R (−)-MDMA trained mice, Journal of Pharmacology and Experimental Therapeutics, Nov. 1, 2009, pp. 717-723.
Murnane, et al., Endocrine and neurochemical effects of 3,4-methylenedioxymethamphetamine and its stereoisomers in rhesus monkeys, Journal of Pharmacology and Experimental Therapeutics, Aug. 1, 2010, pp. 642-650.
Murnane, et al., The neuropharmacology of prolactin secretion elicited by 3, 4-methylenedioxymethamphetamine ("ecstasy"): a concurrent microdialysis and plasma analysis study, Hormones and behavior, Feb. 1, 2012, pp. 181-190.
Mustafa, et al., Review Paper: MDMA and the Brain: A Short Review on the Role of Neurotransmitters in Neurotoxicity, Basic and Clinical Neuroscience, 2020, pp. 381-388.
Nair et al., "Fully Validated, Multi-Kilogram cGMP Synthesis of MDMA", ACS Omega, Dec. 20, 2021, vol. 7, 1, pp. 900-907.
Nichols, D.E., et al., "Derivatives of 1-(1,3-benzodioxol-5-yl)-2-butanamine: representatives of a novel therapeutic class," Journal of Medicinal Chemistry, Oct. 1986, vol. 29 (10), pp. 2009-2015.
Nie, et al., Synthesis of fluorodopamines: effect of aryl fluoro substituents on affinities for adrenergic and dopaminergic receptors, Medicinal Chemistry Research, Jan. 1996, pp. 318-332.
Organic Chemistry Portal "Amino Protecting Groups Stability", (1999), pp. 1-3.
Peters, et al., Concentrations and ratios of amphetamine, methamphetamine, MDA, MDMA, and MDEA enantiomers determined in plasma samples from clinical toxicology and driving under the influence of drugs cases by GC-NICI-MS, Journal of Analytical Toxicology, Nov. 1, 2003, pp. 552-559.
Peters, et al., Drug testing in blood: validated negative-ion chemical ionization gas chromatographic-mass spectrometric assay for determination of amphetamine and methamphetamine enantiomers and its application to toxicology cases, Clinical Chemistry, Sep. 1, 2002, pp. 1472-1485.
Peters, et al., Negative-ion chemical ionization gas chromatography-mass spectrometry assay for enantioselective measurement of amphetamines in oral fluid: application to a controlled study with MDMA and driving under the influence cases, Clinical chemistry, Apr. 1, 2007 A, pp. 702-710.
Pitts et al., (±)-MDMA and its enantiomers: potential therapeutic advantages of R(−)-MDMA, Psychopharmacology, 2018, pp. 377-392.
Pizarro, et al., Stereochemical analysis of 3,4-methylenedioxymethamphetamine and its main metabolites in human samples including the catechol-type metabolite (3,4-dihydroxymethamphetamine), Drug Metabolism and Disposition, Sep. 1, 2004, pp. 1001-1007.
Pizarro et al., "Synthesis and Capillary Electrophoretic Analysis of Enantiomerically Enriched Reference Standards of MDMA and its Main Metabolites," Bioorganic & Medicinal Chemistry (2002) 10: 1085-1092.
PUBCHEM, SID 235735835, Available Date: Feb. 13, 2015 [retrieved on Apr. 23, 2023], 8 pages. Retrieved from: https://pubchem.ncbi.nlm.nih.gov/substance/235735835.
PUBCHEM, SID 243280603, Modify Date: Jun. 24, 2015 [retrieved on Dec. 27, 2022, 7 pages. Retrieved: https://pubchem.ncbi.nlm.nih.gov/substance/243280603].
PUBCHEM, Substance Record for SID 38492237, Dec. 5, 2007, 5 pages.
PUBCHEM, Substance Record for SID 406789554, Jul. 18, 2020, 6 pages.
PUBCHEM, Substance Record for SID 439624087, Jan. 15, 2021, 6 pages.
Pubill, et al., Neuronal nicotinic receptors as new targets for amphetamine-induced oxidative damage and neurotoxicity, Pharmaceuticals, Jun. 15, 2011, pp. 822-847.
Rickli, et al., Pharmacological profile of novel psychoactive benzofurans, British Journal of Pharmacology, Jul. 2015, pp. 3412-3425.
Rothman, et al., Amphetamine-type central nervous system stimulants release norepinephrine more potently than they release dopamine and serotonin, Synapse, Jan. 1, 2001, pp. 32-41.
Rudnick, et al., The molecular mechanism of "ecstasy" [3, 4-methylenedioxy-methamphetamine (MDMA)]: serotonin transporters are targets for MDMA-induced serotonin release, Proceedings of the National Academy of Sciences, Mar. 1, 1992, pp. 1817-1821.
Schwaninger, et al., Development and validation of LC-HRMS and GC-NICI-MS methods for stereoselective determination of MDMA and its phase I and II metabolites in human urine, Journal of Mass Spectrometry, Jul. 2011, pp. 603-614.
Schwaninger, et al., Stereoselective urinary MDMA (ecstasy) and metabolites excretion kinetics following controlled MDMA administration to humans, Biochemical pharmacology, Jan. 1, 2012, pp. 131-138.
Setola, et al., 3, 4-methylenedioxymethamphetamine (MDMA, "Ecstasy") induces fenfluramine-like proliferative actions on human cardiac valvular interstitial cells in vitro, Molecular Pharmacology, Jun. 1, 2003, pp. 1223-1229.
Steele, et al., Stereochemical effects of 3,4-methylenedioxymethamphetamine (MDMA) and related amphetamine derivatives on inhibition of uptake of [3H] monoamines into synaptosomes from different regions of rat brain, Biochemical Pharmacology, Jul. 15, 1987, pp. 2297-2303.
Strajhar, et al., Effects of lisdexamfetamine on plasma steroid concentrations compared with d-amphetamine in healthy subjects: A randomized, double-blind, placebo-controlled study, The Journal of steroid biochemistry and molecular biology, Feb. 2019, pp. 212-225.
Substance Record for SID 104098418 to PubChem, Jan. 2011, 6 pages.
Substance Record for SID 117678335 to PubChem, Apr. 2011, 6 pages.
Sun, et al., Facile and universal immobilization of L-lysine inspired by mussels, J. Mater. Chem., 2012, Journal of Materials Chemistry, 2012, pp. 10035-10041.
Thomas, et al., Characterization of 3, 4-methylenedioxypyrovalerone discrimination in female Sprague-Dawley rats, Behavioural Pharmacology, Jul. 2021, pp. 524-532.
Thomsen, et al., In Vitro Drug Metabolism by Human Carboxylesterase 1: Focus on Angiotensin-Converting Enzyme Inhibitors, Drug Metabolism and Disposition, Jan. 2014, pp. 126-133.

(56) References Cited

OTHER PUBLICATIONS

Tournier, et al., Interaction of drugs of abuse and maintenance treatments with human P-glycoprotein (ABCB1) and breast cancer resistance protein (ABCG2), International Journal of Neuropsychopharmacology, Aug. 1, 2010, pp. 905-915.

United States Patent and Trademark Office, International Search Report and Written Opinion for International Application No. PCT/US2022/045587 dated Feb. 1, 2023, 25 pages.

United States Patent and Trademark Office, International Search Report and Written Opinion for International Application No. PCT/US2022/077432 dated Dec. 15, 2022, 14 pages.

Verrico, et al., MDMA (Ecstasy) and human dopamine, norepinephrine, and serotonin transporters: implications for MDMA-induced neurotoxicity and treatment, Psychopharmacology, Jan. 2007, pp. 489-503.

Verweij, A., "Impurities in illicit drug preparations; 3,4-methylenedioxyamphetamine and 3-4-methylenedioxymethylamphetamine", Forensic. Sci. Rev., 1992, pp. 1-6.

Weinstock, et al., Ecstasy pill testing: harm minimization gone too far?, Addiction, 2001, pp. 1139-1148.

Weinstock, et al., Synthesis and renal vasodilator activity of some dopamine agonist 1-aryl-2,3,4,5-tetrahydro-1H-3-benzazepine-7,8-diols: halogen and methyl analogs of fenoldopam, Journal of Medicinal Chemistry, 1986, pp. 2315-2325.

Wu, et al., Estimation of tamoxifen metabolite concentrations in the blood of breast cancer patients through CYP2D6 genotype activity score, Breast Cancer Research and Treatment, 2012, pp. 677-683.

Young, et al., MDMA (N-methyl-3,4-methylenedioxyamphetamine) and its Stereoisomers: Similarities and Differences in Behavioral Effects in an Automated Activity Apparatus in Mice, Pharmacol Biochem Behav., Jan. 2008, pp. 318-331.

Anderson, et al., "Absolute configuration and psychotomimetic activity", NIDA Res Monogr. 1978, vol. (22), pp. 8-15.

Green et al., "The pharmacology and clinical pharmacology of 3,4-methylenedioxymethamphetamine (MDMA, "ecstasy")", Pharmacol Rev, Sep. 2003; 55(3): 463-508. Epub Jul. 17, 2003.

International Search Report and Written Opinion for Application No. PCT/US2022/042353, dated Dec. 8, 2022, and received Dec. 13, 2022, 9 pages.

* cited by examiner

SYNTHESIS OF MDMA OR ITS OPTICALLY ACTIVE (R)- OR (S)-MDMA ISOMERS

CROSS-REFERENCE TO RELATED APPLICATIONS

The present Application claims priority to U.S. Provisional Patent Application No. 63/239,853 filed Sep. 1, 2021, and which is hereby incorporated by reference in its entirety.

BACKGROUND

MDMA (3,4-methylenedioxymethamphetamine) is considered the prototype of a class of compounds called entactogens, which means "to touch within", their main characteristic being their ability to increase feelings of love, empathy and closeness towards others. Structurally, MDMA is a ring-substituted phenethylamine with a chiral molecular center that gives rise to two stereoisomers: S-(+)-MDMA and R-(−)-MDMA. Typically, effects of the former resemble those of psychostimulants and are primarily mediated by dopaminergic and noradrenergic pathways, including increases in motor activity and euphoria, whereas the latter induces qualitative effects similar to classical psychedelics, such as ego-dissolution and perceptive alterations, mediated by serotonergic pathways, including direct 5-HT2A receptor agonism. The molecular mechanisms for these differences are supported by preclinical evidence and point to a higher therapeutic index for the R-enantiomer.

There remains a need for improved processes of making MDMA (3,4-methylenedioxymethamphetamine) and pharmaceutically acceptable salts thereof and enantiomers thereof.

SUMMARY

In an aspect, the present disclosure provides a process for the preparation of 3,4-methylenedioxymethamphetamine (MDMA). In some embodiments, the present disclosure provides a process for the preparation of racemic 3,4-methylenedioxymethamphetamine (MDMA). In some embodiments, the present disclosure provides a process for the preparation of enantiopure (R) or (S) 3,4-methylenedioxymethamphetamine (MDMA).

In embodiments, the present disclosure provides: a process for the preparation of 3,4-methylenedioxymethamphetamine, or a pharmaceutically acceptable salt thereof, the process comprising:
i) preparing an organometallic reagent from a compound of Formula (I):

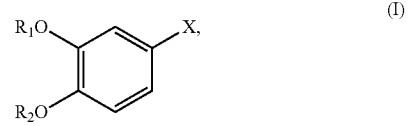

wherein X is a halogen; $R_1$ is a protecting group, $R_2$ is a protecting group or $R_1$ and $R_2$ together with the atoms to which they are attached form a 5-membered heterocycle;
ii) reacting the organometallic reagent of step i) with a compound of Formula (IIb):

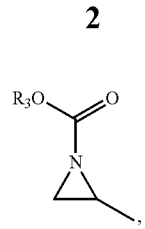

wherein $R_3$ is alkyl; and
iii) converting the product of step ii) to 3,4-methylenedioxymethamphetamine.

In embodiments, the compound of Formula (IIb) is racemic.

In embodiments, the present disclosure provides: a process for the preparation of (S)-3,4-methylenedioxymethamphetamine, or a pharmaceutically acceptable salt thereof, the process comprising:
i) preparing an organometallic reagent from a compound of Formula (I):

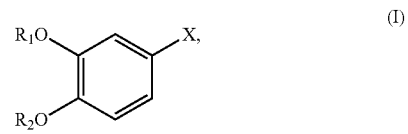

wherein X is a halogen; $R_1$ is a protecting group, $R_2$ is a protecting group or $R_1$ and $R_2$ together with the atoms to which they are attached form a 5-membered heterocycle;
ii) reacting the organometallic reagent of step i) with a compound of Formula (II):

wherein $R_3$ is alkyl; and
iii) converting the product of step ii) to (S)-3,4-methylenedioxymethamphetamine.

In some embodiments, the present disclosure provides: a process for the preparation of (R)-3,4-methylenedioxymethamphetamine, or a pharmaceutically acceptable salt thereof, the process comprising:
i) preparing an organometallic reagent from a compound of Formula (I):

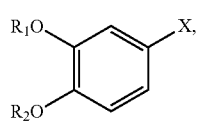

wherein X is a halogen; $R_1$ is a protecting group, $R_2$ is a protecting group or $R_1$ and $R_2$ together with the atoms to which they are attached form a 5-membered heterocycle;
ii) reacting the organometallic reagent of step i) with a compound of Formula (IIa):

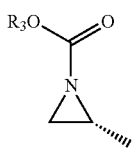

(IIa)

wherein $R_3$ is alkyl; and iii) converting the product of step ii) to (R)-3,4-methylenedioxymethamphetamine.

In some embodiments, X is preferably bromine.

In some embodiments, the process provides 3,4-methylenedioxymethamphetamine, or a pharmaceutically acceptable salt in as a racemate.

In some embodiments, the process provides (S)-3,4-methylenedioxymethamphetamine, or a pharmaceutically acceptable salt in an enantiomeric excess of a least 99.5%.

In some embodiments, the process provides (R)-3,4-methylenedioxymethamphetamine, or a pharmaceutically acceptable salt in an enantiomeric excess of a least 99.5%.

DETAILED DESCRIPTION

Throughout this disclosure, various patents, patent applications and publications are referenced. The disclosures of these patents, patent applications and publications in their entireties are incorporated into this disclosure by reference for all purposes in order to more fully describe the state of the art as known to those skilled therein as of the date of this disclosure. This disclosure will govern in the instance that there is any inconsistency between the patents, patent applications and publications cited and this disclosure.

Definitions

For convenience, certain terms employed in the specification, examples and claims are collected here. Unless defined otherwise, all technical and scientific terms used in this disclosure have the same meanings as commonly understood by one of ordinary skill in the art to which this disclosure belongs.

The term "about" when immediately preceding a numerical value means a range (e.g., plus or minus 10% of that value). For example, "about 50" can mean 45 to 55, "about 25,000" can mean 22,500 to 27,500, etc., unless the context of the disclosure indicates otherwise, or is inconsistent with such an interpretation. For example in a list of numerical values such as "about 49, about 50, about 55, . . . ", "about 50" means a range extending to less than half the interval(s) between the preceding and subsequent values, e.g., more than 49.5 to less than 50.5. Furthermore, the phrases "less than about" a value or "greater than about" a value should be understood in view of the definition of the term "about" provided herein. Similarly, the term "about" when preceding a series of numerical values or a range of values (e.g., "about 10, 20, 30" or "about 10-30") refers, respectively to all values in the series, or the endpoints of the range.

The term "pharmaceutically acceptable salts" includes both acid and base addition salts. Pharmaceutically acceptable salts include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. The acids that may be used to prepare pharmaceutically acceptable acid addition salts of such basic compounds are those that form non-toxic acid addition salts, i.e., salts containing pharmaceutically acceptable anions, including but not limited to malate, oxalate, chloride, bromide, iodide, nitrate, acetate, tartrate, oleate, fumarate, formate, benzoate, glutamate, methanesulfonate, benzenesulfonate, and p-toluenesulfonate salts. Base addition salts include but are not limited to, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris-(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine dicyclohexylamine and the like. Examples of metal salts include lithium, sodium, potassium, magnesium, calcium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like. Those skilled in the art will further recognize that acid addition salts may be prepared by reaction of the compounds with the appropriate inorganic or organic acid via any of a number of known methods.

When a range of values is listed, it is intended to encompass each value and sub-range within the range. For example, "$C_1$-$C_6$ alkyl" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" or "alkyl group" refers to a fully saturated, straight or branched hydrocarbon chain having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_5$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Heterocyclyl," "heterocyclic ring" or "heterocycle" refers to a stable saturated, unsaturated, or aromatic 3- to 20-membered ring which consists of two to nineteen carbon atoms and from one to six heteroatoms selected from the group consisting of nitrogen, oxygen and sulfur, and which is attached to the rest of the molecule by a single bond. Heterocyclyl or heterocyclic rings include heteroaryls, heterocyclylalkyls, heterocyclylalkenyls, and heterocyclylalkynyls. Unless stated otherwise specifically in the specification, the heterocyclyl can be a monocyclic, bicyclic, tricyclic or tetracyclic ring system, which can include fused, bridged, or spirocyclic ring systems; and the nitrogen, carbon or sulfur atoms in the heterocyclyl can be optionally oxidized; the nitrogen atom can be optionally quaternized; and the heterocyclyl can be partially or fully saturated. Examples of such heterocyclyl include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group can be optionally substituted.

The term "substituted" used herein means any of the groups described herein (e.g., alkyl, heterocyclyl, and/or heteroaryl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(O)R_h$, —$NR_gC(=O)NR_gR_h$, —$NR_gC(O)OR_g$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

As used herein, the symbol "⊢" (hereinafter can be referred to as "a point of attachment bond") denotes a bond that is a point of attachment between two chemical entities, one of which is depicted as being attached to the point of attachment bond and the other of which is not depicted as being attached to the point of attachment bond. For example,

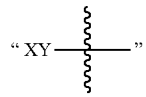

indicates that the chemical entity "XY" is bonded to another chemical entity via the point of attachment bond. Furthermore, the specific point of attachment to the non-depicted chemical entity can be specified by inference. For example, the compound $CH_3$—$R^{3X}$, wherein $R^{3X}$ is H or

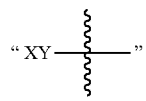

infers that when $R^{3X}$ is "XY", the point of attachment bond is the same bond as the bond by which $R^{3X}$ is depicted as being bonded to $CH_3$.

Methods

In an aspect, the methods described herein provide high purity, 3,4-methylenedioxymethamphetamine (MDMA) in a high yielding 3-step process, starting from readily available and inexpensive starting materials (e.g., 5-bromobenzo[d][1,3]dioxole (3) and alaninol). In an aspect, the disclosure provides a process for preparation of racemic 3,4-methylenedioxymethamphetamine or a pharmaceutically acceptable salt thereof.

In an aspect, the disclosure provides a process for the preparation of (R)- or (S)-3,4-methylenedioxymethamphetamine, or a pharmaceutically acceptable salt thereof.

In embodiments, the methods described herein provide high purity, enantiopure (R) or (S) 3,4-methylenedioxymethamphetamine (MDMA) in a high yielding 3-step process, starting from readily available and inexpensive starting materials (e.g., 5-bromobenzo[d][1,3]dioxole (3) and D-alaninol (1)). By starting with a chiral pool starting materials, such as (D-alaniol (1)), enantiopure (R)-MDMA can be prepared without the need for expensive and wasteful chiral ligands, chiral auxiliaries, or diastereomeric salt resolutions, and provide MDMA with higher optical purity (e.g., 99.5% ee or greater, or 99.9% ee) than other routes, which give lower selectivity and require enantiomeric enrichment by purification/crystallization. By installing a Boc group as both a nitrogen protecting group and a masked methyl equivalent, the need for a methylation reaction is avoided, which often uses GTI alkylating reagents like methyl iodide or dimethylsulfate. It also cleanly installs the single methyl group and avoids the potential of over-alkylation and provides enantioenriched (R)-MDMA in a streamlined process, providing significant improvements on prior syntheses which are more complex and/or require synthetic longer routes see e.g., *ACS Chem Neurosci.* 2018 Oct. 17; 9(10): 2408-2427. The unnatural enantiomer of (1) (L-alaninol) can be used by the same process to prepare (S)-MDMA.

Preparation of
3,4-methylenedioxymethamphetamine

In an aspect, the disclosure provides a process for the preparation of 3,4-methylenedioxymethamphetamine, or a pharmaceutically acceptable salt thereof, the process comprising:

i) preparing an organometallic reagent from a compound of Formula (I):

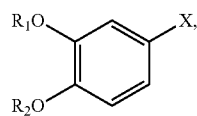
(I)

wherein X is a halogen; $R_1$ is a protecting group, $R_2$ is a protecting group or $R_1$ and $R_2$ together with the atoms to which they are attached form a 5-membered heterocycle;

ii) reacting the organometallic reagent of step i) with a compound of Formula (IIb):

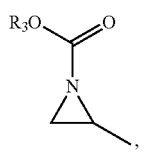
(IIb)

wherein $R_3$ is alkyl; and iii) converting the product of step ii) to 3,4-methylenedioxymethamphetamine.

In embodiments, the compound of Formula (IIb) is a racemate.

In embodiments of the processes provided herein for the preparation of 3,4-methylenedioxymethamphetamine, the process comprises i) preparing an organometallic reagent from a compound of Formula (I):

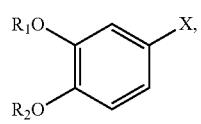
(I)

wherein X is a halogen; $R_1$ is a protecting group, $R_2$ is a protecting group or $R_1$ and $R_2$ together with the atoms to which they are attached form a 5-membered heterocycle.

In some embodiments of any one of the processes for the preparation of 3,4-methylenedioxymethamphetamine described herein, $R_1$ and $R_2$ together with the atoms to which they are attached form a 5-membered heterocycle.

In some embodiments of the process for the preparation of 3,4-methylenedioxymethamphetamine, the compound of Formula (I) is a compound of Formula (Ia):

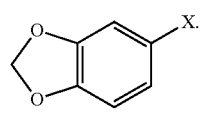
(Ia)

In embodiments of the compounds of Formula (I) or (Ia), X is Cl, Br, or I. In some embodiments, X is Cl. In some embodiments, X is Br. In some embodiments, X is I.

In some embodiments of the process for the preparation of 3,4-methylenedioxymethamphetamine, step i) comprises reacting the compound of Formula (I) or Formula (Ia) with magnesium. In some embodiments, step i) comprises reacting the compound of Formula (I) or Formula (Ia) with magnesium in the presence of a solvent, for example an ether solvent such as tetrahydrofuran, diethyl ether, or 2-methyltetrahydrofuran. In some embodiments, the solvent is heated e.g., to 50-70° C., 60-70° C., or 60-66° C. In some embodiments, the solvent is heated to reflux. In some embodiments, the solvent is THF and the THF is heated to reflux.

In some embodiments of the process for the preparation of 3,4-methylenedioxymethamphetamine, step i) further comprises adding a copper (I) salt (e.g., CuI, CuCl, or CuBr·SMe$_2$) to the reaction mixture. In some embodiments, after formation of the Grignard species, the solution is cooled, and copper iodide (CuI) is added. In some embodiments, the solution is cooled for example, to a temperature between 0° C. and −78° C. and copper iodide (CuI) is added. In some embodiments, the organometallic reagent selectively opens the aziridine at the less hindered carbon, retaining the stereochemistry of the nitrogen stereocenter to give carbamate protected methylenedioxyamphetamine.

In embodiments of the process for the preparation of 3,4-methylenedioxymethamphetamine, step ii) comprises reacting the organometallic reagent of step i) with a compound of Formula (IIb):

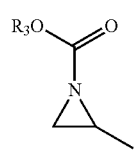
(IIb)

wherein $R_3$ is alkyl. In some embodiments, step ii) comprises adding a compound of Formula (IIb) to the cooled solution of organometallic reagent from step i).

In some embodiments of the process for the preparation of 3,4-methylenedioxymethamphetamine, $R_3$ is $C_{1-6}$ alkyl. In some embodiments, $R_3$ is $C_{1-4}$ alkyl. In some embodiments, $R_3$ is tert-butyl.

In some embodiments of the process for the preparation of 3,4-methylenedioxymethamphetamine, the product of step ii) is a compound of Formula (IIIb):

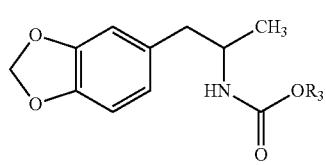
(IIIb)

wherein $R_3$ is defined herein.

In some embodiments of the process for the preparation of 3,4-methylenedioxymethamphetamine, the product of step ii) is a compound of Formula (IIIc):

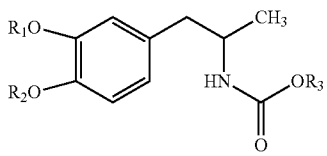

(IIIc)

wherein $R_1$, $R_2$, and $R_3$ are defined herein.

In some embodiments of the process for the preparation of 3,4-methylenedioxymethamphetamine, step iii) comprises reacting a group of Formula (IVb) with a reducing agent to provide a group of Formula (Vb), or a pharmaceutically acceptable salt thereof:

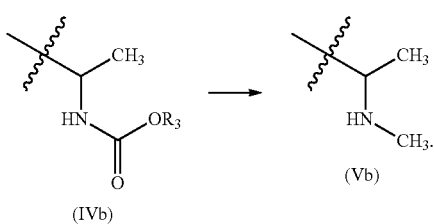

(IVb) (Vb)

In some embodiments, step iii) comprises reacting a group of Formula (IVb) with a reducing agent to provide a group of Formula (Vb), or a pharmaceutically acceptable salt thereof in the presence of a solvent, for example an ether solvent such as tetrahydrofuran, diethyl ether, 2-methyltetrahydrofuran. In some embodiments, the solvent is heated. In some embodiments, the solvent is refluxing THF.

In some embodiments of the process for the preparation of 3,4-methylenedioxymethamphetamine, the reducing agent in step iii) is a hydride reducing agent. In some embodiments, the reducing agent in step iii) is lithium aluminum hydride.

In some embodiments of the process for the preparation of 3,4-methylenedioxymethamphetamine, the process provides 3,4-methylenedioxymethamphetamine, or a pharmaceutically acceptable salt thereof in racemic form.

In some embodiments of the process for the preparation of 3,4-methylenedioxymethamphetamine, the 3,4-methylenedioxymethamphetamine, or a pharmaceutically acceptable salt thereof has a chemical purity of greater than about 95%, greater than about 98%, or greater than about 99% by HPLC.

In some embodiments, the present disclosure provides 3,4-methylenedioxymethamphetamine, or a pharmaceutically acceptable salt prepared by a process described herein.

Preparation of (S)-3,4-methylenedioxymethamphetamine

In an aspect, the disclosure provides a process for the preparation of (S)-3,4-methylenedioxymethamphetamine, or a pharmaceutically acceptable salt thereof, the process comprising:
i) preparing an organometallic reagent from a compound of Formula (I):

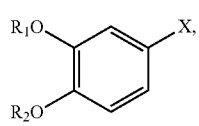

(I)

wherein X is a halogen; $R_1$ is a protecting group, $R_2$ is a protecting group or $R_1$ and $R_2$ together with the atoms to which they are attached form a 5-membered heterocycle;

ii) reacting the organometallic reagent of step i) with a compound of Formula (II):

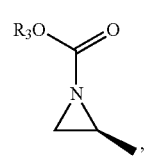

(II)

wherein $R_3$ is alkyl; and iii) converting the product of step ii) to (S)-3,4-methylenedioxymethamphetamine.

In embodiments of the processes provided herein for the preparation of (S)-3,4-methylenedioxymethamphetamine, the process comprises i) preparing an organometallic reagent from a compound of Formula (I):

(I)

wherein X is a halogen; $R_1$ is a protecting group, $R_2$ is a protecting group or $R_1$ and $R_2$ together with the atoms to which they are attached form a 5-membered heterocycle.

In some embodiments of any one of the processes for the preparation of (S)-3,4-methylenedioxymethamphetamine described herein, $R_1$ and $R_2$ together with the atoms to which they are attached form a 5-membered heterocycle.

In some embodiments of the process for the preparation of (S)-3,4-methylenedioxymethamphetamine, the compound of Formula (I) is a compound of Formula (Ia):

(Ia)

In embodiments of the compounds of Formula (I) or (Ia), X is Cl, Br, or I. In some embodiments, X is Cl. In some embodiments, X is Br. In some embodiments, X is I.

In some embodiments of the process for the preparation of (S)-3,4-methylenedioxymethamphetamine, step i) comprises reacting the compound of Formula (I) or Formula (Ia) with magnesium. In some embodiments, step i) comprises reacting the compound of Formula (I) or Formula (Ia) with magnesium in the presence of a solvent, for example an ether solvent such as tetrahydrofuran, diethyl ether, 2-methyltetrahydrofuran. In some embodiments, the solvent is heated e.g., to 50-70° C., or 60-70° C., or 60-66° C. In some embodiments, the solvent is heated to reflux. In some embodiments, the solvent is THF and the THF is heated to reflux.

In some embodiments of the process for the preparation of (S)-3,4-methylenedioxymethamphetamine, step i) further comprises adding a copper (I) salt (e.g., CuI, CuCl, CuBr·SMe$_2$) to the reaction mixture. In some embodiments, after formation of the Grignard species, the solution is cooled, and copper iodide (CuI) is added. In some embodiments, the solution is cooled for example, to a temperature between 0° C. and −78° C. and copper iodide (CuI) is added. In some embodiments, the organometallic reagent selectively opens the aziridine at the less hindered carbon, retaining the stereochemistry of the nitrogen stereocenter to give carbamate protected methylenedioxyamphetamine.

In embodiments of the process for the preparation of (S)-3,4-methylenedioxymethamphetamine, step ii) comprises reacting the organometallic reagent of step i) with a compound of Formula (II):

wherein R$_3$ is alkyl. In some embodiments, step ii) comprises adding a compound of Formula (II) to the cooled solution of organometallic reagent from step i).

In some embodiments of the process for the preparation of (S)-3,4-methylenedioxymethamphetamine, R$_3$ is C$_{1-6}$ alkyl. In some embodiments, R$_3$ is C$_{1-4}$ alkyl. R$_3$ is tert-butyl.

In some embodiments of the process for the preparation of (S)-3,4-methylenedioxymethamphetamine, the product of step ii) is a compound of Formula (III):

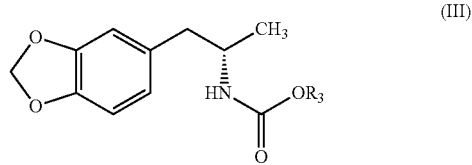

wherein R$_3$ is defined herein.

In some embodiments of the process for the preparation of (S)-3,4-methylenedioxymethamphetamine, the product of step ii) is a compound of Formula (IIIa):

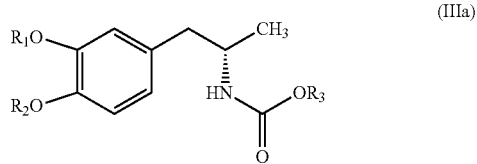

wherein R$_1$, R$_2$, and R$_3$ are defined herein.

In some embodiments of the process for the preparation of (S)-3,4-methylenedioxymethamphetamine, step iii) comprises reacting a group of Formula (IV) with a reducing agent to provide a group of Formula (V), or a pharmaceutically acceptable salt thereof:

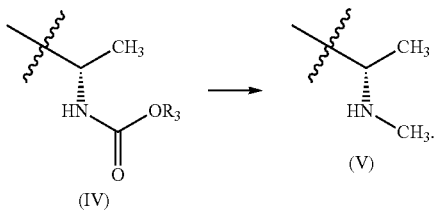

In some embodiments, step iii) comprises reacting a group of Formula (IV) with a reducing agent to provide a group of Formula (V), or a pharmaceutically acceptable salt thereof in the presence of a solvent, for example an ether solvent such as tetrahydrofuran, diethyl ether, 2-methyltetrahydrofuran. In some embodiments, the solvent is heated. In some embodiments, the solvent is refluxing THF.

In some embodiments of the process for the preparation of (S)-3,4-methylenedioxymethamphetamine, the reducing agent in step iii) is a hydride reducing agent. In some embodiments, the reducing agent in step iii) is lithium aluminum hydride.

In some embodiments of the process for the preparation of (S)-3,4-methylenedioxymethamphetamine, the process provides (S)-3,4-methylenedioxymethamphetamine, or a pharmaceutically acceptable salt thereof in substantially optically pure form. In some embodiments, the process for the preparation of (S)-3,4-methylenedioxymethamphetamine, the process provides (S)-3,4-methylenedioxymethamphetamine, or a pharmaceutically acceptable salt in an enantiomeric excess of about or at least about 55% ee, about or at least about 60% ee, about or at least about 65% ee, about or at least about 70% ee, about or at 75% ee, about or at least about 80% ee, about or at least about 85% ee, about or at least about 90% ee, about or at least about 91%, about or at least about 92%, about or at least about 93% ee, about or at least about 94% ee, about or at least about 95% ee, about or at least about 96% ee, about or at least about 97% ee, about or at least about 98% ee, about or at least about 99% ee, about or at least about 99.5% ee, or about or at least about 99.9% ee, including all subranges and values therebetween. In some embodiments, the process for the preparation of (S)-3,4-methylenedioxymethamphetamine, the process provides (S)-3,4-methylenedioxymethamphetamine, or a pharmaceutically acceptable salt in an enantiomeric excess of a least 99.5%. In some embodiments, ee is measured by chiral HPLC.

In some embodiments of the process for the preparation of (S)-3,4-methylenedioxymethamphetamine, the (S)-3,4-methylenedioxymethamphetamine, or a pharmaceutically acceptable salt thereof has a chemical purity of greater than about 95%, greater than about 98%, or greater than about 99% by HPLC.

In some embodiments, the present disclosure provides (S)-3,4-methylenedioxymethamphetamine, or a pharmaceutically acceptable salt prepared by a process described herein.

Preparation of
(R)-3,4-methylenedioxymethamphetamine

In an aspect, the disclosure provides a process or the preparation of (R)-3,4-methylenedioxymethamphetamine, or a pharmaceutically acceptable salt thereof, the method comprising:

i) preparing an organometallic reagent from a compound of Formula (I):

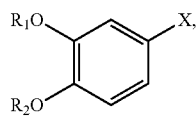

wherein X is a halogen; $R_1$ is a protecting group, $R_2$ is a protecting group or $R_1$ and $R_2$ together with the atoms to which they are attached form a 5-membered heterocycle;

ii) reacting the organometallic reagent of step i) with a compound of Formula (IIa):

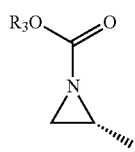

wherein $R_3$ is alkyl; and iii) converting the product of step ii) to (R)-3,4-methylenedioxymethamphetamine.

In embodiments of the processes provided herein for the preparation of (R)-3,4-methylenedioxymethamphetamine, the process comprises i) preparing an organometallic reagent from a compound of Formula (I):

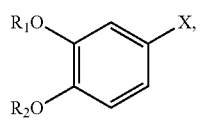

wherein X is a halogen; $R_1$ is a protecting group, $R_2$ is a protecting group or $R_1$ and $R_2$ together with the atoms to which they are attached form a 5-membered heterocycle.

In some embodiments of any one of the processes for the preparation of (R)-3,4-methylenedioxymethamphetamine described herein, $R_1$ and $R_2$ together with the atoms to which they are attached form a 5-membered heterocycle.

In some embodiments of the process for the preparation of (R)-3,4-methylenedioxymethamphetamine, the compound of Formula (I) is a compound of Formula (Ia):

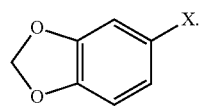

In embodiments of the compounds of Formula (I) or (Ia), X is Cl, Br, or I. In some embodiments, X is Cl. In some embodiments, X is Br. In some embodiments, X is I.

In some embodiments of the process for the preparation of (R)-3,4-methylenedioxymethamphetamine, step i) comprises reacting the compound of Formula (I) or Formula (Ia) with magnesium. In some embodiments, step i) comprises reacting the compound of Formula (I) or Formula (Ia) with magnesium in the presence of a solvent, for example an ether solvent such as tetrahydrofuran, diethyl ether, 2-methyltetrahydrofuran. In some embodiments, the solvent is heated e.g., to 50-70° C. In some embodiments, the solvent is THF and the THF is heated to reflux.

In some embodiments of the process for the preparation of (R)-3,4-methylenedioxymethamphetamine, step i) further comprises adding a copper (I) salt (e.g., CuI, CuCl, CuBr·SMe$_2$) to the reaction mixture. In some embodiments, after formation of the Grignard species, the solution is cooled, and copper iodide (CuI) is added. In some embodiments, the solution is cooled for example, to a temperature between 0° C. and –78° C. and copper iodide (CuI) is added. In some embodiments, the organometallic reagent selectively opens the aziridine at the less hindered carbon, retaining the stereochemistry of the nitrogen stereocenter to give carbamate protected methylenedioxyamphetamine.

In some embodiments of the process for the preparation of (R)-3,4-methylenedioxymethamphetamine, step ii) comprises reacting the organometallic reagent of step i) with a compound of Formula (IIa):

wherein $R_3$ is alkyl. In some embodiments, step ii) comprises adding a compound of Formula (IIa) to the cooled solution of organometallic reagent from step i).

In some embodiments of the process for the preparation of (R)-3,4-methylenedioxymethamphetamine, $R_3$ is $C_{1-6}$ alkyl. In some embodiments, $R_3$ is $C_{1-4}$ alkyl. $R_3$ is tert-butyl.

In some embodiments of the process for the preparation of (R)-3,4-methylenedioxymethamphetamine, the product of step ii) is a compound of Formula (IIIb):

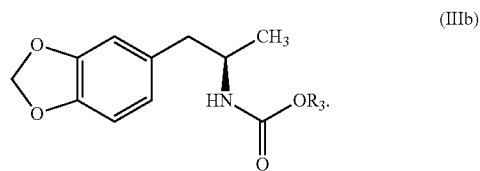

In some embodiments of the process for the preparation of (R)-3,4-methylenedioxymethamphetamine, the product of step ii) is a compound of Formula (IIIb'):

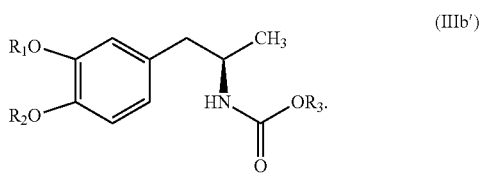

In some embodiments of the process for the preparation of (R)-3,4-methylenedioxymethamphetamine, step iii) comprises reacting a group of Formula (IVa) with a reducing agent to provide a group of Formula (Va), or a pharmaceutically acceptable salt thereof:

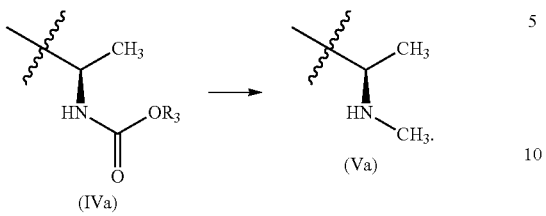

In some embodiments, step iii) comprises reacting a group of Formula (IV) with a reducing agent to provide a group of Formula (V), or a pharmaceutically acceptable salt thereof in the presence of a solvent, for example an ether solvent such as tetrahydrofuran, diethyl ether, 2-methyltetrahydrofuran.

In some embodiments of the process for the preparation of (R)-3,4-methylenedioxymethamphetamine, the reducing agent in step iii) is a hydride reducing agent. In some embodiments, the reducing agent in step iii) is lithium aluminum hydride.

In some embodiments of the process for the preparation of (R)-3,4-methylenedioxymethamphetamine, the process provides (R)-3,4-methylenedioxymethamphetamine, or a pharmaceutically acceptable salt thereof in substantially optically pure form. In some embodiments, the process for the preparation of (R)-3,4-methylenedioxymethamphetamine, the process provides (R)-3,4-methylenedioxymethamphetamine, or a pharmaceutically acceptable salt in an enantiomeric excess of about or at least about 55% ee, about or at least about 60% ee, about or at least about 65% ee, about or at least about 70% ee, about or at 75% ee, about or at least about 80% ee, about or at least about 85% ee, about or at least about 90% ee, about or at least about 91%, about or at least about 92%, about or at least about 93% ee, about or at least about 94% ee, about or at least about 95% ee, about or at least about 96% ee, about or at least about 97% ee, about or at least about 98% ee, about or at least about 99% ee, about or at least about 99.5% ee, or about or at least about 99.9% ee, including all subranges and values therebetween. In some embodiments, the process for the preparation of (R)-3,4-methylenedioxymethamphetamine, the process provides (R)-3,4-methylenedioxymethamphetamine, or a pharmaceutically acceptable salt in an enantiomeric excess of a least 99.5%. In some embodiments, ee is measured by chiral HPLC.

In some embodiments of the process for the preparation of (R)-3,4-methylenedioxymethamphetamine, the (R)-3,4-methylenedioxymethamphetamine, or a pharmaceutically acceptable salt thereof has a chemical purity of greater than about 95%, greater than about 98%, or greater than about 99% by HPLC.

In some embodiments, the present disclosure provides (R)-3,4-methylenedioxymethamphetamine, or a pharmaceutically acceptable salt prepared by a process described herein.

NUMBERED EMBODIMENTS

1. A process for the preparation of (S)-3,4-methylenedioxymethamphetamine, or a pharmaceutically acceptable salt thereof, the process comprising:

i) preparing an organometallic reagent from a compound of Formula (I):

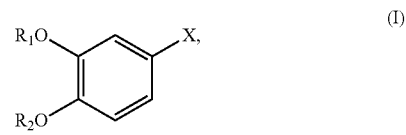

wherein X is a halogen; $R_1$ is a protecting group, $R_2$ is a protecting group or $R_1$ and $R_2$ together with the atoms to which they are attached form a 5-membered heterocycle;

ii) reacting the organometallic reagent of step i) with a compound of Formula (II):

wherein $R_3$ is alkyl; and iii) converting the product of step ii) to (S)-3,4-methylenedioxymethamphetamine.

2. The process of embodiment 1, wherein the compound of Formula (I) is a compound of Formula (Ia):

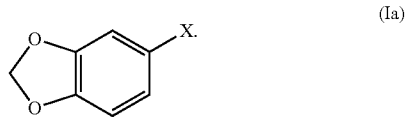

3. The process of embodiment 2, wherein X is bromine.
4. The process of any one of embodiments 1-3, wherein $R_3$ is tert-butyl.
5. The process of any one of embodiments 1-4, wherein step i) comprises reacting the compound of Formula (I) or Formula (Ia) with magnesium.
6. The process of embodiment 5, wherein the step i) further comprises adding a copper (I) salt (e.g., CuI) to the reaction mixture.
7. The process of any one of embodiments 1-6, wherein the product of step ii) is a compound of Formula (III):

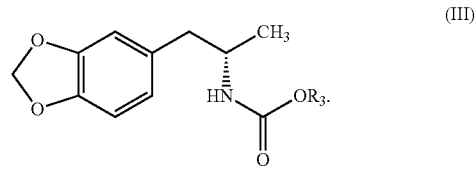

8. The process of any one of embodiments 1-6, wherein the product of step ii) is a compound of Formula (IIIa):

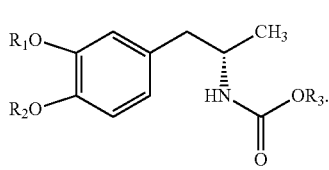

(IIIa)

9. The process of any one of embodiments 1-8, wherein the step iii) comprises reacting a group of Formula (IV) with a reducing agent to provide a group of Formula (V), or a pharmaceutically acceptable salt thereof:

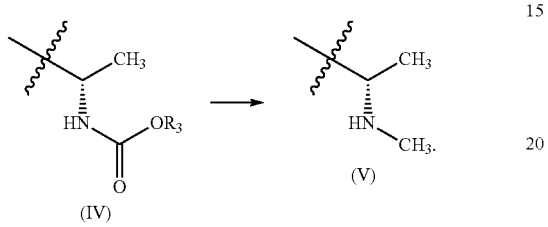

10. The process of embodiment 9, wherein the reducing agent is lithium aluminum hydride.
11. The process of any one of embodiments 1-10, wherein the process provides (S)-3,4-methylenedioxymethamphetamine, or a pharmaceutically acceptable salt in an enantiomeric excess of a least 99.5%.
12. (S)-3,4-methylenedioxymethamphetamine, or a pharmaceutically acceptable salt prepared by a process of any one of embodiments 1-10.
13. A process for the preparation of (R)-3,4-methylenedioxymethamphetamine, or a pharmaceutically acceptable salt thereof, the process comprising:
   i) preparing an organometallic reagent from a compound of Formula (I):

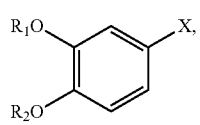

(I)

wherein X is a halogen; $R_1$ is a protecting group, $R_2$ is a protecting group or $R_1$ and $R_2$ together with the atoms to which they are attached form a 5-membered heterocycle;
   ii) reacting the organometallic reagent of step i) with a compound of Formula (IIa):

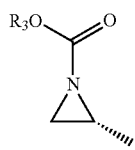

(IIa)

wherein $R_3$ is alkyl; and
   iii) converting the product of step ii) to (R)-3,4-methylenedioxymethamphetamine.
14. The process of embodiment 13, wherein the compound of Formula (I) is a compound of Formula (Ia):

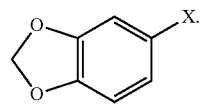

(Ia)

15. The process of any one of embodiments 13-14, wherein X is bromine.
16. The process of any one of embodiments 13-15, wherein $R_3$ is tert-butyl.
17. The process of any one of embodiments 13-16, wherein step i) comprises reacting the compound of Formula (I) or Formula (Ia) with magnesium.
18. The process of embodiment 17, wherein the step i) further comprises adding a copper (I) salt (e.g., CuI) to the reaction mixture.
19. The process of any one of embodiments 13-18, wherein the product of step ii) is a compound of Formula (IIIb):

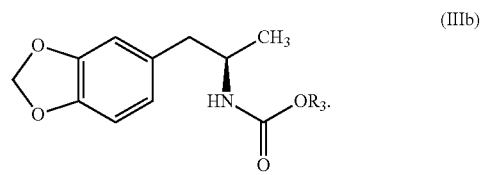

(IIIb)

20. The process of any one of embodiments 13-18, wherein the product of step ii) is a compound of Formula (IIIb'):

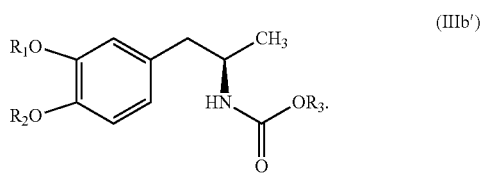

(IIIb')

21. The process of any one of embodiments 13-20, wherein the step iii) comprises reacting a group of Formula (IVa) with a reducing agent to provide a group of Formula (Va), or a pharmaceutically acceptable salt thereof:

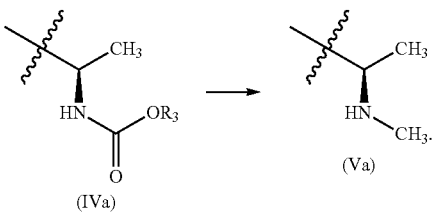

22. The process of embodiment 21, wherein the reducing agent is lithium aluminum hydride.
23. The process of any one of embodiments 13-22, wherein the process provides (R)-3,4-methylenedioxymethamphetamine, or a pharmaceutically acceptable salt in an enantiomeric excess of a least 99.5%.
24. (R)-3,4-methylenedioxymethamphetamine, or a pharmaceutically acceptable salt prepared by a process of any one of embodiments 13-23.

25. A process for the preparation of 3,4-methylenedioxymethamphetamine, or a pharmaceutically acceptable salt thereof, the process comprising:
   i) preparing an organometallic reagent from a compound of Formula (I):

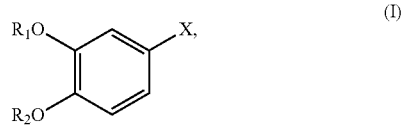

wherein X is a halogen; $R_1$ is a protecting group, $R_2$ is a protecting group or $R_1$ and $R_2$ together with the atoms to which they are attached form a 5-membered heterocycle;
   ii) reacting the organometallic reagent of step i) with a compound of Formula (II):

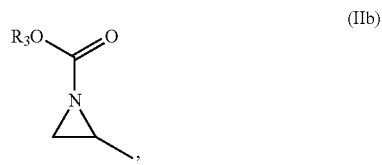

wherein $R_3$ is alkyl; and
   iii) converting the product of step ii) to 3,4-methylenedioxymethamphetamine.
26. The process of embodiment 25, wherein the compound of Formula (I) is a compound of Formula (Ia):

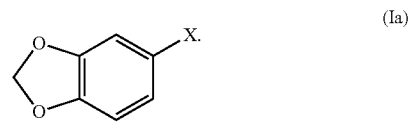

27. The process of embodiment 26, wherein X is bromine.
28. The process of any one of embodiments 25-27, wherein $R_3$ is tert-butyl.
29. The process of any one of embodiments 25-28, wherein step i) comprises reacting the compound of Formula (I) or Formula (Ia) with magnesium.
30. The process of embodiment 29, wherein the step i) further comprises adding a copper (I) salt (e.g., CuI) to the reaction mixture.
31. The process of any one of embodiments 25-30, wherein the product of step ii) is a compound of Formula (III):

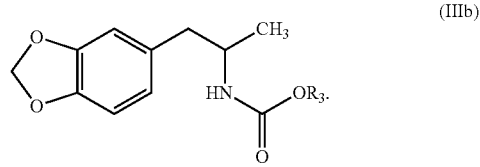

32. The process of any one of embodiments 25-30, wherein the product of step ii) is a compound of Formula (IIIc):

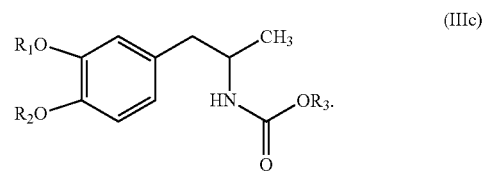

33. The process of any one of embodiments 1-8, wherein the step iii) comprises reacting a group of Formula (IVb) with a reducing agent to provide a group of Formula (Vb), or a pharmaceutically acceptable salt thereof:

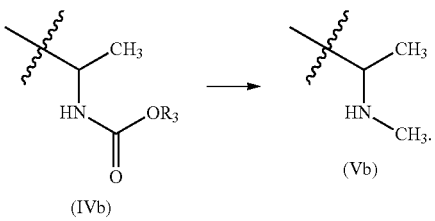

34. The process of embodiment 33, wherein the reducing agent is lithium aluminum hydride.
35. The process of any one of embodiments 25-34, wherein the process provides (S)-3,4-methylenedioxymethamphetamine, or a pharmaceutically acceptable salt in an enantiomeric excess of a least 99.5%.
36. 3,4-methylenedioxymethamphetamine, or a pharmaceutically acceptable salt prepared by a process of any one of embodiments 25-35.

EXAMPLES

Compounds of the present disclosure can be synthesized using the following exemplary methods or other methods that are known to those skilled in the art.

General reaction conditions are provided, and reaction products can be purified by known methods including silica gel chromatography using various organic solvents such as hexane, dichloromethane, ethyl acetate, methanol and the like or preparative reverse phase high pressure liquid chromatography.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene and Wuts, *Protective Groups in Organic Synthesis*, 44th. Ed., Wiley & Sons, 2006, as well as in Jerry March, *Advanced Organic Chemistry*, 4th edition, John Wiley & Sons, publisher, New York, 1992 which are incorporated herein by reference in their entirety.

General Synthesis of
(R)-3,4-methylenedioxymethamphetamine (MDMA)

(R)-3,4-methylenedioxymethamphetamine (MDMA) can be synthesized according to Scheme 1, below.

Scheme 1

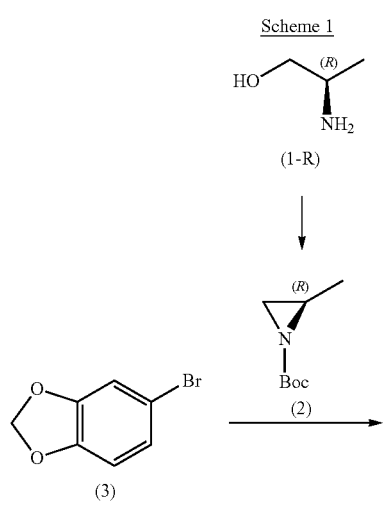

(4)

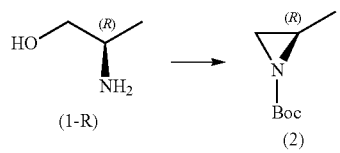

(R)-MDMA

Step 1: Synthesis of tert-butyl (R)-2-methylaziridine-1-carboxylate (2)

D-alaninol (1) is protected with di-tert-butyl decarbonate (Boc anhydride) in organic solvent (e.g., halogenated solvent such as dichloromethane (DCM), ether solvent such as tetrahydrofuran (THF) or methyl-tetrahydrofuran (Me-THF)) e.g. at <about 10° C. to ambient temperature, over a few hours. To the protected D-alaninol is then added 4-toluenesulfonyl chloride (TsCl), followed by potassium hydroxide (KOH), which installs the tosyl group on the alcohol, and deprotonates the carbamate nitrogen, facilitating aziridine formation. The enantiopure aziridine (2) is then isolated and purified, e.g., by chromatography on SiO$_2$ or by distillation.

Step 2: Synthesis of tert-butyl (R)-(1-(benzo[d][1,3]dioxol-5-yl)propan-2-yl)carbamate (4)

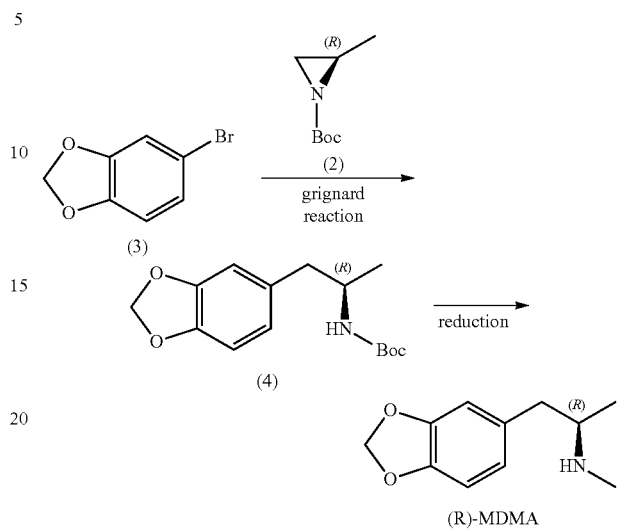

In a second step, the Grignard reagent of 5-bromobenzo[d][1,3]dioxole (3) is generated by treatment of 5-bromobenzo[d][1,3]dioxole (3) with magnesium, optionally in the presence of I$_2$, in organic solvent (e.g., ether solvent such as tetrahydrofuran (THF) or methyl-tetrahydrofuran (Me-THF)) and the mixture heated, e.g., between about 40° C. to about 70° C., or about 50° C. to about 60° C. After formation of the Grignard species, the solution is cooled (e.g., to about 0° C. or less) and Copper (I) salt e.g., CuI or CuBr·SMe$_2$ is added. The previously isolated Boc-aziridine (2) is then added to the cooled solution of cuprate and stirred until the reaction is complete. The reaction is then quenched with an aqueous solution e.g., with NH$_4$Cl and the organic phase extracted with organic solvent and purified by chromatography on SiO$_2$, or by crystallization.

Step 3: Synthesis of (R)-3,4-methylenedioxymethamphetamine (MDMA)

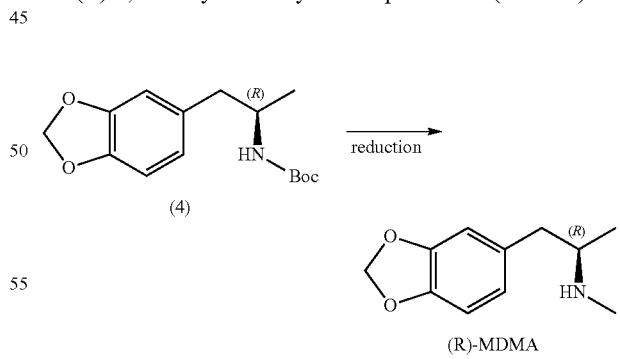

The Boc-MDA (4) is then dissolved in organic solvent (e.g., in an ether solvent such as tetrahydrofuran, (THF) or 2-methyltetrahydrofuran (Me-THF)), cooled and treated with lithium aluminum hydride (LiAlH4) to reduce the carbamate to the methylamine. In some embodiments, the solution is heated (e.g., to reflux) to reduce the carbamate to the methylamine. The reaction is quenched and worked-up via the Fieser method with water, NaOH and methyl tert-butyl ether. The crude MDMA free base can then be isolated e.g., by crystallization, or converted into the HCl salt using a solution of HCl.

(S)-3,4-methylenedioxymethamphetamine (MDMA) can be synthesized according to Scheme 1 employing L-alaninol instead of D-alaninol.

Example 1: Synthesis of (R)-3,4-methylenedioxymethamphetamine (MDMA)

(R)-3,4-methylenedioxymethamphetamine (MDMA) can be synthesized according to the Scheme below.

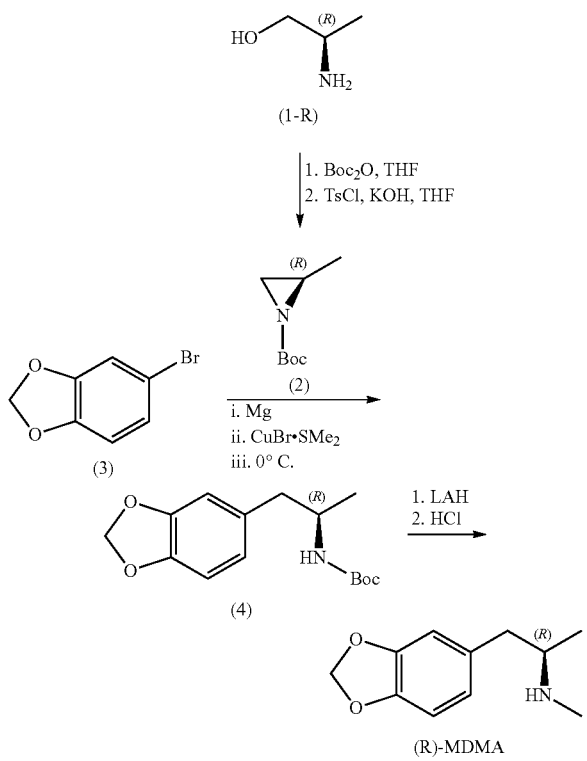

Step 1, Route 1: Synthesis of tert-butyl (R)-2-methylaziridine-1-carboxylate

To a 300 mL jacketed reactor was charged D-alaninol (20 g, 266.3 mmol, 1.00 eq) and DCM (100 mL) then cooled to 0-5° C. under N$_2$. A solution of Boc$_2$O (64.2 g, 292.9 mmol, 1.1 eq) in DCM (100 mL) was added over 40 minutes maintaining an internal temperature of <12° C. After the addition was complete the reaction was warmed to 20° C. After 3.5 hours no D-alaninol was detected by TLC. The reaction was diluted with water (50 mL), then the organic layer was washed with sat. NaCl (2×50 mL), dried over MgSO$_4$, filtered and concentrated under reduced pressure to afford crude Boc-D-alaninol (62.2 g). The crude product was charged to the 300 mL reactor as a solution in THF (200 mL) at 20° C. Solid TsCl (66.2 g, 1.3 eq) was charged resulting in a 10° C. endotherm. Solid powdered KOH (60.1 g, 4.0 eq) was added in portions—the initial KOH charge resulted in a strong exotherm (>20° C.), requiring setting the TCU to 0° C. Subsequent charges only saw <5° C. exotherms. As the mixture cooled to <30° C. the reaction was held at 20° C. After 20 minutes the mixture became very thick and a further 100 mL of THF was added to aid mixing. After stirring for 21 hours the mixture was filtered and the filter cake washed with MTBE. The filtrate was concentrated under reduced pressure to afford crude compound 2 (52.1 g). Chromatographic purification on silica (600 g), eluting with 0-60% EtOAc/heptanes afforded compound 2 (13.1 g, 31%) as a light yellow oil.

Step 1, Route 2: Synthesis of tert-butyl (R)-2-methylaziridine-1-carboxylate

To a 250 mL RBF was charged D-alaninol (EMP-2, 5.0 g, 66.6 mmol, 1.00 eq) and THF (33 mL) then cooled to 0-5° C. under N$_2$. A solution of Boc$_2$O (14.9 g, 67.9 mmol, 1.02 eq) in THF (7.5 mL) was added over 50 minutes maintaining an internal temperature of <10° C. After the addition was complete the reaction was warmed to 15° C. After 16 hours no D-alaninol was detected by TLC. A solution of TsCl (17.8 g, 1.4 eq) in THF (10 mL) was added at 15° C., resulting in a 3° C. endotherm, followed by a THF (2.5 mL) rinse. Solid powdered KOH (18.3 g, 4.9 eq) was added resulting in a strong exotherm (>35° C.), requiring external cooling. The reaction mixture became white slurry. After stirring for 22 hours the mixture was diluted with MTBE (25 mL, 5 vol), filtered and the filter cake washed with MTBE. The filtrate was passed through a silica plug (30 g), eluting with MTBE to afford compound 2 (7.37 g, 57%).

Step 2: Synthesis of tert-butyl (R)-(1-(benzo[d][1,3] dioxol-5-yl)propan-2-yl)carbamate (4)

To a 100 mL RBF was charged Mg (0.155 g, 6.36 mmol, 2.00 eq), I$_2$ (one crystal) and THF (3 mL) at room temperature under N$_2$. Bromide 3 (0.1 g) was added to the mixture and heated to 50° C. at which time the iodine color disappeared and the internal temperature rose to 56° C. Bromide 3 (1.20 g, total added 1.30 g, 6.46 mmol, 2.0 eq) was added, via syringe, to the mixture dropwise maintaining an internal temperature of 45-55° C. over 10 minutes. After addition was complete the syringe was rinsed with THF (0.5 mL) and the rinse charged to the reaction at 49° C. After stirring for 1.5 hours the batch was a clear amber color with an internal temperature of 19.6° C. THF (2.0 mL) was added. The flask was cooled to 0.8° C. using an ice/water bath then solid CuBr·SMe$_2$ (0.131 g, 0.636 mmol, 0.20 eq) was charged in one portion. An exotherm to 6° C. was observed. After cooling to 0.5° C. a solution of R-Boc-aziridine 2 (87.8 wt %, 0.57 g, 3.18 mmol, 1.00 eq) in THF (1.5 mL) was added over 20 minutes, while maintaining an internal temperature <6° C. After stirring for 4 hours TLC analysis (5:1 heptanes/ EA) of the brown slurry showed complete reaction. After a further 20 minutes the reaction was quenched with dropwise addition sat. NH$_4$Cl (5.0 mL), while maintaining an internal temperature <18° C. (3 minutes). After stirring for 12 minutes at room temperature the biphasic mixture was diluted with EtOAc (3 mL). The layers were separated, and the aqueous layer was extracted with EtOAc (2×3 mL). The combined organic layers dried over Na$_2$SO$_4$ (2.5 g), filtered and concentrated under reduced pressure. Chromatographic purification in silica, eluting with 0-15% EtOAc/heptanes afforded compound 4 (0.77 g, 87%) as a solid.

Step 3: Synthesis of (R)-3,4-methylenedioxymethamphetamine (MDMA)

To a 5-neck 2 L jacketed reactor was charged compound 4 (78.3 g, 280.6 mmols, 1.0 eq) and THF (1.4 L, 18 vol). The solution is heated to 55 to 60° C. and a solution of lithium aluminum hydride (LAH, 2 M in THF, 430 mL, 842 mmols, 3.0 eq) is slowly added over 1.5 hours, maintaining an internal temperature of 55 to 65° C. After 1 hour, IPC analysis by HPLC showed 0.6% compound 4 remaining. After an additional 2 hours, IPC analysis showed 0.5% compound 4 remaining. The batch was cooled to 0 to 5° C. and 32 mL of water was slowly charged over ~80 minutes, keeping the reaction temperature below 15° C. 15% NaOH (32 mL) was then added over 8 minutes, followed by water (96 mL). The thick slurry was warmed to ambient temperature and stirred overnight. The slurry was filtered, and the filter cake washed with methyl tert-butyl ether (2×2 vol). The filtrate was concentrated under reduced pressure to afford crude (R)-MDMA (54.0 g) which was diluted with MeOH (118 mL) and MTBE (1.3 L) at ambient temperature under nitrogen. To the solution was added 3M HCl in MeOH (140 mL, 1.5 eq), resulting in the formation of a white slurry. The slurry was stirred for 30 minutes and filtered, and the filter cake was washed with MTBE (3×200 mL). The cake was dried under reduced pressure to afford (R)-MDMA-HCl (55.2 g, 85%) with an HPLC purity of 99.5% area by HPLC.

The invention claimed is:

1. A process for the preparation of 3,4-methylenedioxymethamphetamine, or a pharmaceutically acceptable salt thereof, the process comprising:
   i) preparing an organometallic reagent from a compound of Formula (I):

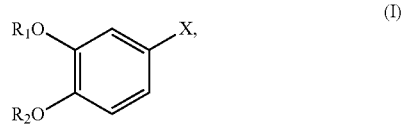

wherein X is a halogen; $R_1$ and $R_2$ together with the atoms to which they are attached form a 1,3-dioxolane;
   ii) reacting the organometallic reagent of step i) with a compound of Formula (II):

wherein $R_3$ is alkyl; and
   iii) converting the product of step ii) to 3,4-methylenedioxymethamphetamine.

2. The process of claim 1, wherein X is bromine.
3. The process of claim 1, wherein $R_3$ is tert-butyl.
4. The process of claim 1, wherein step i) comprises reacting the compound of Formula (I) with magnesium.
5. The process of claim 1, wherein step i) comprises reacting the compound of Formula (Ia) with magnesium.
6. The process of claim 1, wherein the step i) further comprises adding a copper (I) salt to the reaction mixture.
7. The process of claim 6, wherein the copper (I) salt is CuI.

8. The process of claim 1, wherein the product of step ii) is a compound of Formula (IIIb):

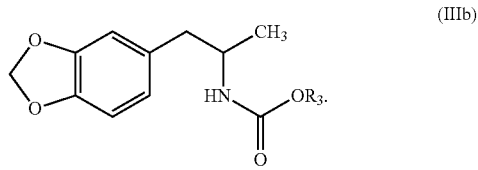

9. The process of claim 1, wherein the step iii) comprises reacting a group of Formula (IVb) with a reducing agent to provide a group of Formula (Vb), or a pharmaceutically acceptable salt thereof:

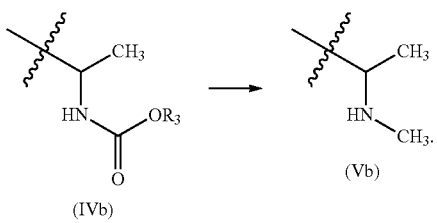

10. The process of claim 9, wherein the reducing agent is lithium aluminum hydride.
11. A process for the preparation of (R)-3,4-methylenedioxymethamphetamine, or a pharmaceutically acceptable salt thereof, the process comprising:
    i) preparing an organometallic reagent from a compound of Formula (I):

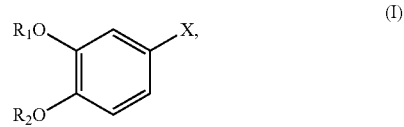

wherein X is a halogen; $R_1$ and $R_2$ together with the atoms to which they are attached form a 1,3-dioxolane;
    ii) reacting the organometallic reagent of step i) with a compound of Formula (IIa):

wherein $R_3$ is alkyl; and
    iii) converting the product of step ii) to (R)-3,4-methylenedioxymethamphetamine.

12. The process of claim 11, wherein X is bromine.
13. The process of claim 11, wherein $R_3$ is tert-butyl.
14. The process of claim 11, wherein step i) comprises reacting the compound of Formula (I) with magnesium.
15. The process of claim 11, wherein step i) comprises reacting the compound of Formula (Ia) with magnesium.
16. The process of claim 11, wherein the step i) further comprises adding a copper (I) salt to the reaction mixture.

17. The process of claim 16, wherein the copper (I) salt is CuI.

18. The process of claim 11, wherein the product of step ii) is a compound of Formula (IIIb):

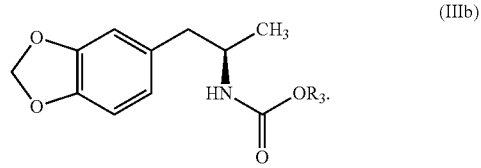

19. The process of claim 11, wherein the step iii) comprises reacting a group of Formula (IVa) with a reducing agent to provide a group of Formula (Va), or a pharmaceutically acceptable salt thereof:

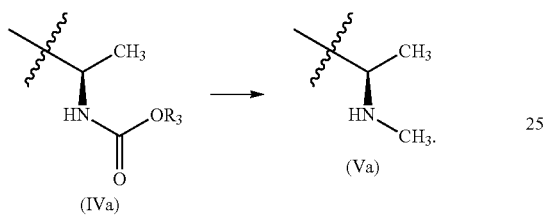

20. The process of claim 19, wherein the reducing agent is lithium aluminum hydride.

21. The process of claim 11, wherein the process provides (R)-3,4-methylenedioxymethamphetamine, or a pharmaceutically acceptable salt in an enantiomeric excess of a least 99.5%.

22. A process for the preparation of (S)-3,4-methylenedioxymethamphetamine, or a pharmaceutically acceptable salt thereof, the process comprising:
  i) preparing an organometallic reagent from a compound of Formula (I):

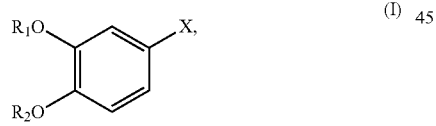

wherein X is a halogen; $R_1$ and $R_2$ together with the atoms to which they are attached form a 1,3-dioxolane;
  ii) reacting the organometallic reagent of step i) with a compound of Formula (II):

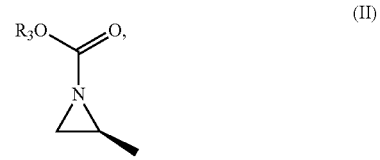

wherein $R_3$ is alkyl; and
  iii) converting the product of step ii) to (S)-3,4-methylenedioxymethamphetamine.

23. The process of claim 22, wherein X is bromine.

24. The process of claim 22, wherein $R_3$ is tert-butyl.

25. The process of claim 22, wherein step i) comprises reacting the compound of Formula (I) with magnesium.

26. The process of claim 22, wherein step i) comprises reacting the compound of Formula (Ia) with magnesium.

27. The process of claim 22, wherein the step i) further comprises adding a copper (I) salt to the reaction mixture.

28. The process of claim 27, wherein the copper (I) salt is CuI.

29. The process of claim 22, wherein the product of step ii) is a compound of Formula (III):

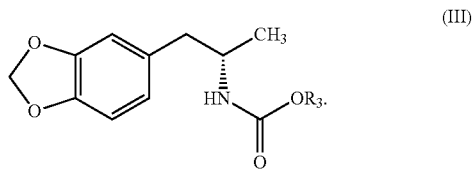

30. The process of claim 22, wherein the step iii) comprises reacting a group of Formula (IV) with a reducing agent to provide a group of Formula (V), or a pharmaceutically acceptable salt thereof:

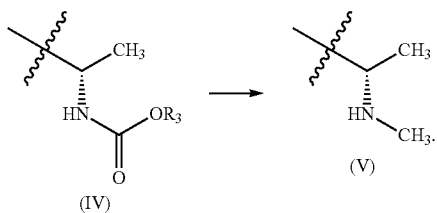

31. The process of claim 30, wherein the reducing agent is lithium aluminum hydride.

32. The process of claim 22, wherein the process provides (S)-3,4-methylenedioxymethamphetamine, or a pharmaceutically acceptable salt in an enantiomeric excess of a least 99.5%.

* * * * *

UNITED STATES PATENT AND TRADEMARK OFFICE
CERTIFICATE OF CORRECTION

PATENT NO. : 11,993,577 B2
APPLICATION NO. : 17/901504
DATED : May 28, 2024
INVENTOR(S) : Majed Fawaz et al.

Page 1 of 5

It is certified that error appears in the above-identified patent and that said Letters Patent is hereby corrected as shown below:

In the Claims

At Column 25, Claim number 1, Line number 33:

" 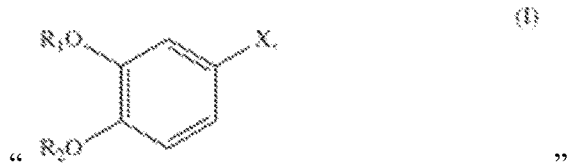 "

Should read:

-- 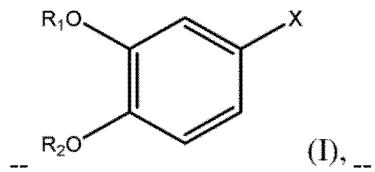 --

At Column 25, Claim number 1, Line number 46:

" 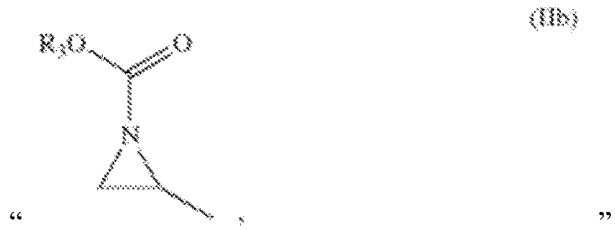 "

Signed and Sealed this
Third Day of September, 2024

*Katherine Kelly Vidal*
Katherine Kelly Vidal
*Director of the United States Patent and Trademark Office*

CERTIFICATE OF CORRECTION (continued)
U.S. Pat. No. 11,993,577 B2

Should read:

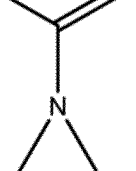

-- (IIb), --

At Column 26, Claim number 8, Line number 5:

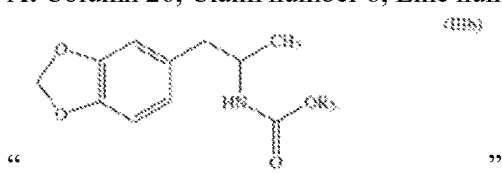

Should read:

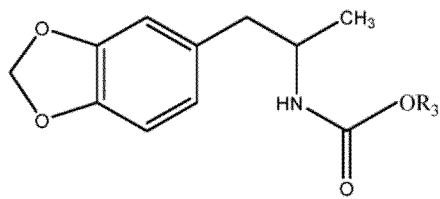

-- (IIIb). --

At Column 26, Claim number 9, Line number 18:

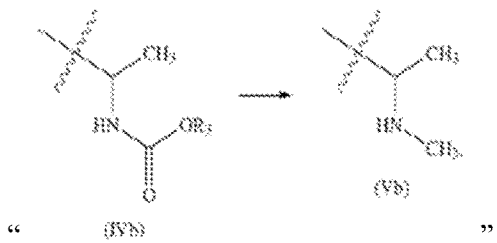

Should read:

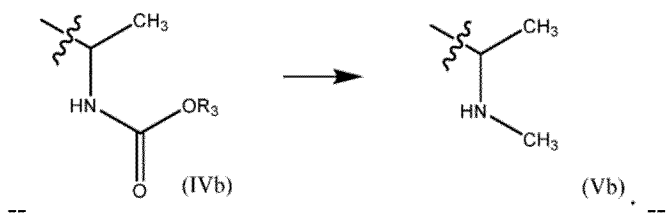

-- . --

At Column 26, Claim number 11, Line number 38:

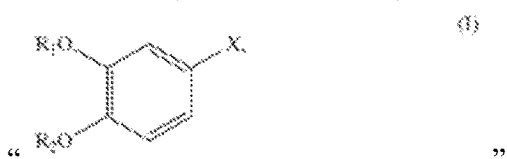

Should read:
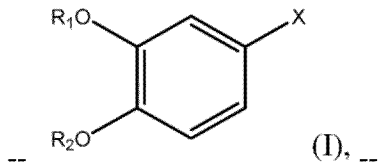   (I), --
At Column 27, Claim number 18, Line number 7:
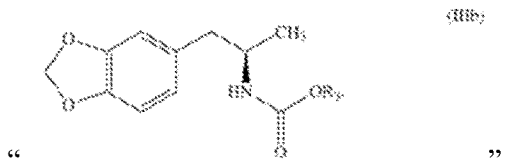
Should read:
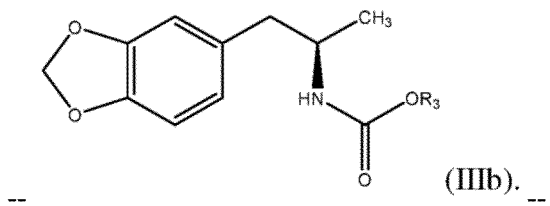   (IIIb). --
At Column 27, Claim number 19, Line number 7:
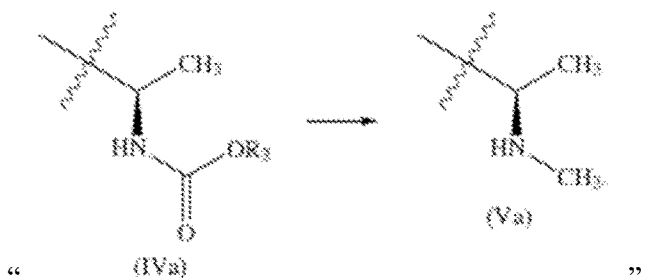
Should read:
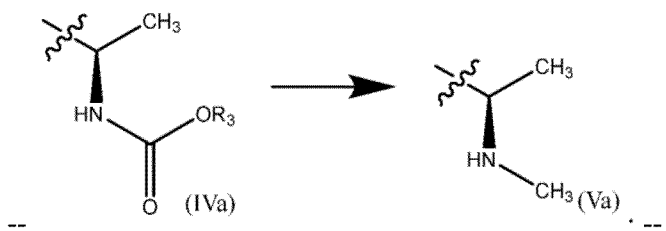   . --
At Column 27, Claim number 22, Line number 44:
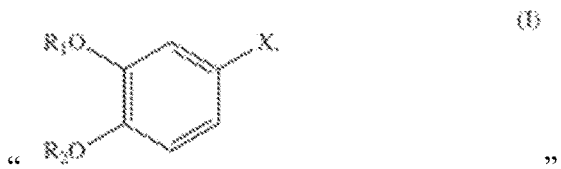

Should read:
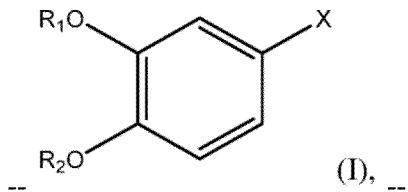
-- (I), --
At Column 28, Claim number 22, Line number 1:
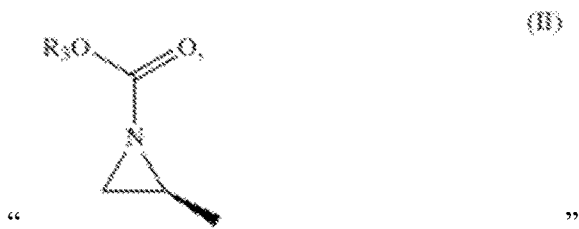
" "
Should read:
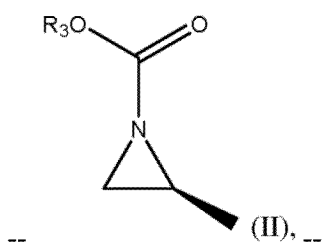
-- (II), --
At Column 28, Claim number 29, Line number 25:
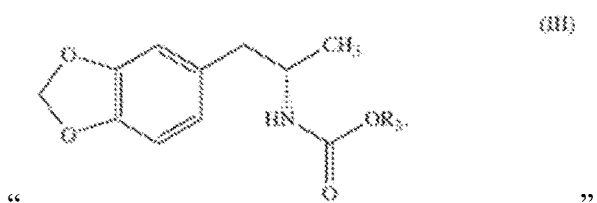
" "
Should read:
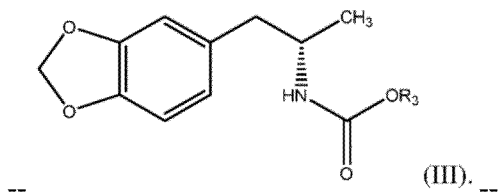
-- (III). --

At Column 28, Claim number 30, Line number 38:
" 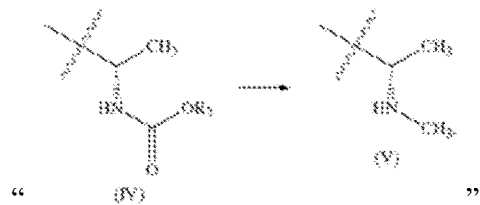 "
Should read:
-- 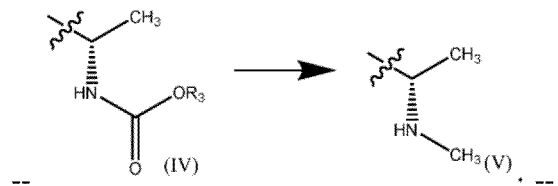 . --